United States Patent [19]
Jonkman

[11] Patent Number: 5,151,087
[45] Date of Patent: Sep. 29, 1992

[54] AORTIC ROOT CANNULA

[75] Inventor: Kenneth R. Jonkman, Grand Rapids, Mich.

[73] Assignee: DLP, Inc., Grand Rapids, Mich.

[21] Appl. No.: 753,038

[22] Filed: Aug. 30, 1991

[51] Int. Cl.$^5$ ............................................. A61M 5/178
[52] U.S. Cl. .................................... 604/164; 604/165;
604/256; 604/51
[58] Field of Search ............... 604/164, 165, 167, 168,
604/169, 44, 45, 35, 126, 256, 51

[56] References Cited

U.S. PATENT DOCUMENTS

| | | | |
|---|---|---|---|
| 4,073,297 | 2/1978 | Kopp | 604/164 |
| 4,096,860 | 6/1978 | McLaughlin | 604/167 |
| 4,531,935 | 7/1985 | Berryessa | 604/164 |
| 4,531,937 | 7/1985 | Yates | 604/164 |
| 4,596,552 | 6/1986 | DeVries | 604/164 |
| 4,723,955 | 2/1988 | Vaillancourt | 604/45 |
| 4,743,243 | 5/1988 | Vaillancourt | 604/45 |
| 4,834,707 | 5/1989 | Evans | 604/164 |
| 4,894,052 | 1/1990 | Crawford | 604/165 |
| 5,013,296 | 5/1991 | Buckberg | 604/164 |

Primary Examiner—Gene Mancene
Assistant Examiner—Michael Lynch
Attorney, Agent, or Firm—Barnes, Kisselle, Raisch, Choate, Whittemore & Hulbert

[57] ABSTRACT

A cannula assembly including a tube cannula and a hollow introducer needle. At the proximal end of the cannula are three fittings: first, a first luer fitting affixed to the proximal end of the tube cannula; second, a luer fitting removably attached to the first luer fitting, this second luer fitting having a first air porous water locking plug at a proximal end penetrated by the needle; and, third, a needle handle removably attachable to the second luer fitting. The proximal end of the needle handle is blocked also by a second air porous water blocking plug. The second plug prevents escape of blood from the hollow needle upon penetration of the arterial wall. The first plug controls the rate of flow of blood to the cannula tube and allows clamping of the tube after withdrawal of the introducer needle and prior to connection to a cardioplegia supply line.

9 Claims, 2 Drawing Sheets

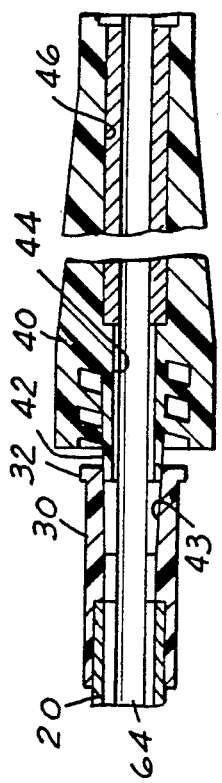
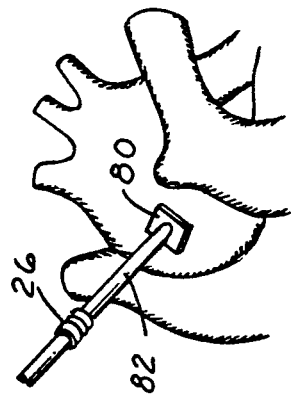
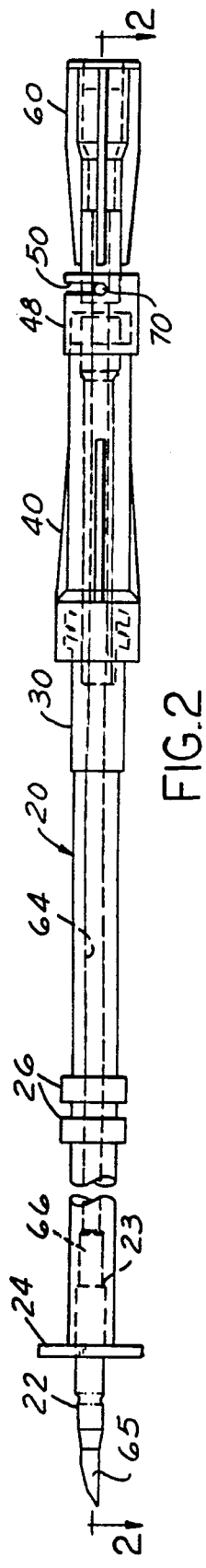
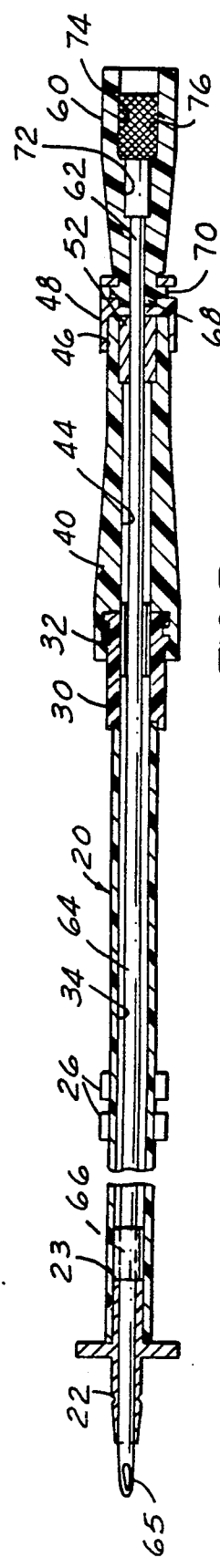
FIG. 1  FIG. 2  FIG. 3  FIG. 4  FIG. 5

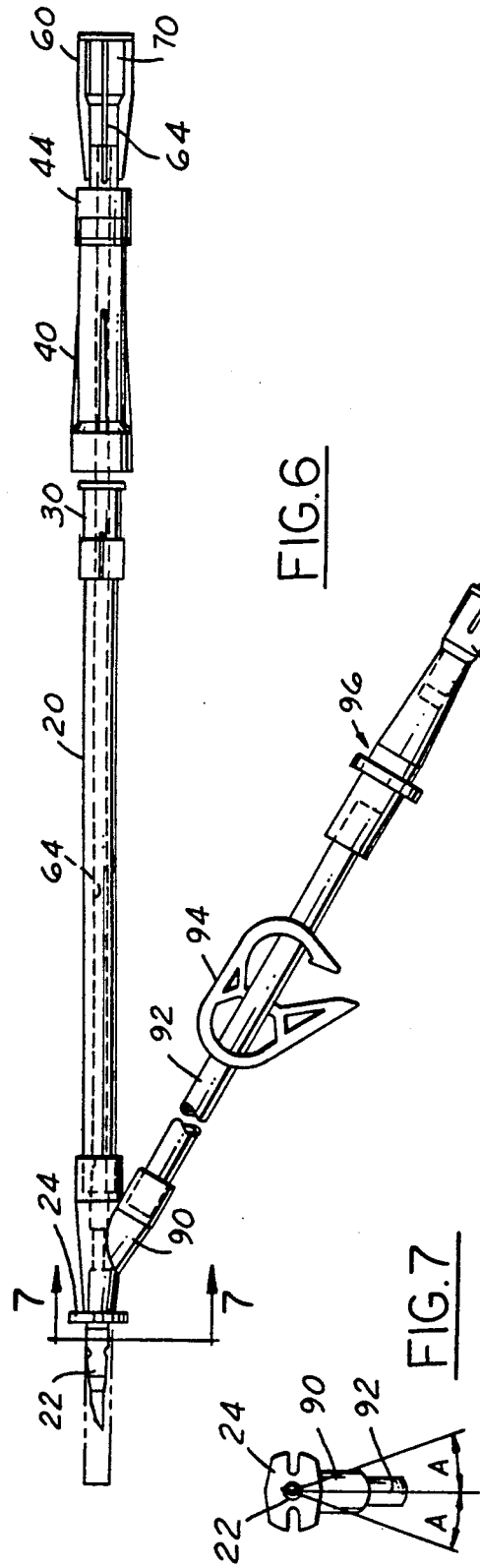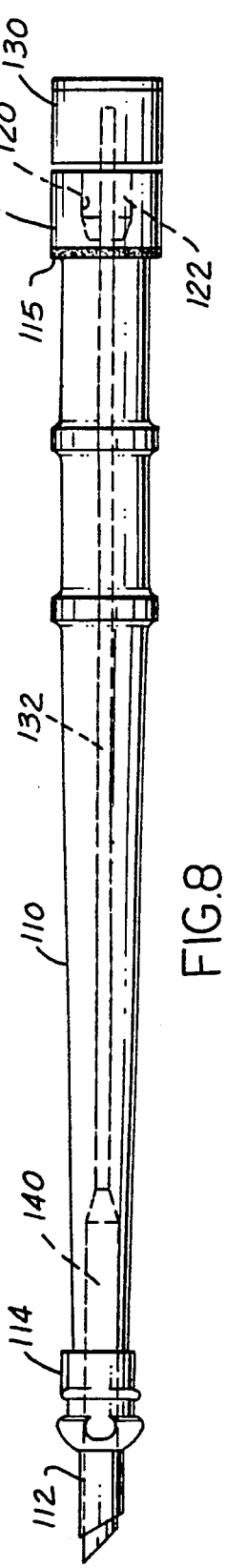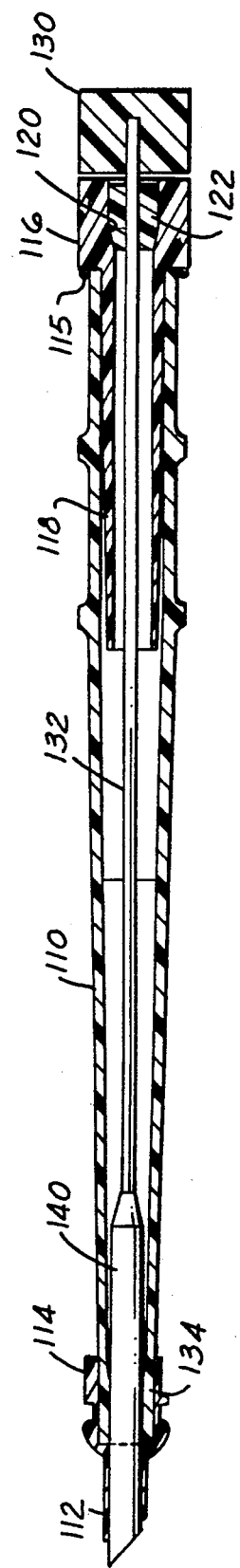

AORTIC ROOT CANNULA

FIELD OF INVENTION

The introduction of cardioplegia liquid into the heart during open heart surgery with the use of a cannula connected to a cardioplegia supply line.

BACKGROUND AND FEATURES OF THE INVENTION

In open heart surgery, it is necessary to by-pass blood from the heart to what is called an "extracorporeal support apparatus" which is also called a life-support system.

Because of its heavy work load and high oxygen requirements, the muscle mass of the heart can tolerate very little ischemia (reduction of blood supply to an area because of obstruction or constriction of the coronary arteries).

A common technique used to protect the ischemic myocardium during the surgery involves the use of induced hypothermic cardioplegia. The technique involves the infusion of a cardioplegic solution into the coronary arteries at a low temperature. The chemical composition of the solution is varied; each cardiovascular surgical team has its own "recipe." However, the one chemical in common to all cardioplegic solutions is potassium. When infused, the potassium causes an immediate arrest of the heart, and the low temperature immediately begins to reduce the heart's oxygen consumption rate. The immediate stoppage and rapid cooling of the myocardium seems to offer the maximum protection available at this time.

In heart surgery, life support machines are utilized to perform temporarily the function of the heart and lungs while the patient's heart is being surgically serviced such as the repair of heart wall lesions, installation of a valve, and bypass artery work. The life support machine must take the flowing blood from the patient, maintain the temperature, pressure, and flow rate within certain physiologic limits, and provide the lung function.

In the course of an operation of this type, it is essential that a change-over be accomplished from the natural heart function to the machine. This involves installation of a venous return catheter into the right atrium (chamber) of the heart to serve as a drainage supply connection to the pumping machine.

In addition to the use of the venous return catheter, it is also necessary to introduce blood from the life support system to the aorta of the heart through an arterial cannula to complete the circuit of the support system during the operation.

Once the change-over to the life support machine is accomplished, the heart must stop beating and be made motionless so that the delicate surgical corrections can be accomplished. To stop the heart, a clamp is placed across the aorta. This cuts off the supply of oxygenated blood to the coronary arteries that supply the heart muscle. The reduced oxygen supply would eventually stop the heart, however, it could also damage the myocardium.

To protect the myocardium, a cooled cardioplegia solution that contains potassium is introduced into the coronary arteries. The potassium causes the heart to arrest and the cooling reduces the oxygen demand and oxygen consumption rate of the heart.

This introduction of the cooled cardioplegic flow is accomplished by the introduction into the aorta of an aortic root cannula which is ultimately secured to the aorta by sutures and connected to the cardioplegia supply line.

The introduction of the aortic cannula is accomplished while blood is still in the heart and it is important that any escape of blood be carefully controlled. This is especially important in recent years due to prevalence of certain blood carrying diseases to which doctors and technicians should not be exposed.

The present invention is directed to the introduction of an aortic root cannula which is designed to allow safe connection of the cardioplegia supply to the aortic part of the heart without the uncontrolled escape of blood to the outside.

It is an object to provide a cannula which will control the vent of air from the cannula and to control the rate at which the pressurized blood fills the cannula. It is also an object to control the flow of blood when the needle introducer is removed in a manner in which the pressurized blood is sealed in the tube prior to disconnection of a luer. A further object lies in the needle design which retracts into a male luer to prevent accidental skin punctures and scratches with a contaminated needle.

In addition to use as an aortic root cannula, the basic device can be used as an arterial cannula using the same introducer system.

Other objects and features of the invention will be apparent in the following description and claims in which the principles of the invention are set forth together with details to enable persons skilled in the art to apply the principles and techniques of the invention, all in connection with the best mode presently contemplated for the invention.

BRIEF DESCRIPTION OF THE DRAWINGS

DRAWINGS accompany the disclosure and the various views thereof may be briefly described as:

FIG. 1, a view of a heart organ with an aortic cannula in place.

FIG. 2, an elevational view of an aortic root cannula.

FIG. 3, a sectional view on line 2—2 of FIG. 2.

FIG. 4, a sectioned view of the assembly with the needle retracted.

FIG. 5, an enlarged sectional view of a male-female connection of adjoining luers.

FIG. 6, a view of an aortic root cannula with a retracting introducer and a vent line.

FIG. 7, a view on line 7—7 of FIG. 6.

FIG. 8, an elevation view of an arterial cannula with an introducer similar to FIGS. 2, 3 and 4.

FIG. 9, a view similar to FIG. 8 with the parts in section.

BRIEF DESCRIPTION OF THE INVENTION

Briefly, the invention comprises an apparatus and a method using a catheter with a suture collar spaced from the tip and male luer fitting carrying a porous blocking bushing capable of passing air and occluding liquid. A hollow needle passes into the catheter through the bushing and this needle has also a blocking plug at the proximal end to prevent escape of blood.

DETAILED DESCRIPTION OF THE INVENTION AND THE MAKING AND THE MANNER AND PROCESS OF USING IT

In FIGS. 2 and 3, a cannula body tube 20 which is flexible and stretchable, has a tapered tip 22 with a back end 23. The cannula tube has a flange 24 and suture collars 26 spaced upwardly from the tip. At the proximal end of the body tube 20 is a female luer fitting 30 with a thread flange 32. The tube 20 has an axial passage 34 which extends from the tip 22 through the fitting 30.

Threaded on the fitting 30 is a male luer fitting 40 which has a threaded recess at the distal end to cooperate with the thread flange 32 on fitting 30. As best shown in FIG. 5, the luer fitting 40 has an axial passage 44 with a small male projection 42 which telescopes into the proximal end 43 of the fitting 30. The fitting 40 has an enlarged cylindrical bore 46 at the proximal end. A lock collar 48 affixed to the proximal end of the fitting 40 has a circumferential slot 50 which has an axial access slot. Positioned within the bore 46 in the male luer fitting 40 is a cylindrically shaped porous bushing 52 press fitted into the bore 46 and designed to pass gas or air but to block the passage of liquid.

Behind the fitting 40 is a needle handle 60 affixed at 62 to the proximal end of a hollow needle 64 which has a sharp end 65 and which has, at its distal end, a stop collar 66. The needle handle 60, which has a clear portion, has a forward plug portion 68 with one or more radial pins 70. This plug portion 68 projects into the collar 48 and, when turned, the pins 70 lock into the groove 50, shown in FIG. 2, to lock the collar 48 and the needle handle 60 axially in place. In this locked position, the needle point 65 projects from the tip 22.

Inside an axial bore 72 in needle handle 60 is a plug recess 74 in which is located a porous plug 76 designed to pass gas or air but to block liquid. The plugs 52 and 76 are preferably formed of a fused high density polypropylene powder with a 3% HPX material. HPX is a water absorbent material, namely, a hydrolized starch polyacrylonitrile graft copolymer. Other parts of the assembly can preferably be formed of plastic such as rigid PVC or Acrylic or flexible PVC. The needle is stainless steel.

While the cannula and needle assembly can be used for a number of applications such as arterial cannulae and any other medical device where an obturator or introducer is used, it is particularly appropriate for use as an aortic root cannula.

To utilize the device, the introducer needle 64 is inserted into the cannula until the stop collar 66 is placed against the back 23 of the tapered tip 22. At this time, luer 40 is locked to the luer 30 and the needle handle is engaged with the lock collar 48 on the luer fitting 40. This insertion and locking stretches the body tube 20 slightly as the male luer 30 is connected to the female luer 40 with the threaded connection 32. A purse string suture using a Teflon pledget 80 is placed at the designed cannulation site (FIG. 1) and the sutures are drawn to a rubber ligature tube 82. With needle end 65 exposed, the needle tip and the cannula tip are inserted into the aorta in the center of the area enclosed by the purse string sutures. When the needle passes through the wall of the aorta and into the bloodstream, pressurized blood fills the needle up to the porous plug 76 in the needle handle 60. The mid-section of the needle handle is clear plastic so that the blood is visible in this section to indicate to the surgeon that the needle is in the bloodstream. The suture ends are then drawn through the slots in the flange 24 and the pledget is placed on top of the flange. The ligature tube is drawn tight and clamped. The ligature tube is tied to the cannula at the rings 26 on the cannula.

Next, the handle 60 is unlocked from the collar 48 by rotation of the locking handle 60 and the introducer needle is drawn smoothly out of the cannula tube 20 to the point that the stop 66 abuts the distal end of the porous plug 52. The retracted position of the needle is shown in FIG. 4. When the needle 64 is withdrawn from the tapered tip 22, pressurized blood can flow into the cannula as the air in the cannula is slowly vented through the porous bushing 52. This bushing has a press-fit with the luer 40 and a slip fit relationship with the needle 64. The sharp needle point 65 is, upon full retraction, in an unexposed position in fitting 40 as shown in FIG. 4. The cannula tube 20 is next pinched or clamped at a convenient, point using suitable clamping means.

When the clamping is accomplished, the female luer 30 is removed from the male luer 40 and the introducer needle 64 is removed from the cannula. The next step in the process is to connect the luer 30 to a cardioplegia delivery circuit while taking the necessary precautions to remove any entrapped air by backbleeding from the aortic root.

A first advantage of the described introducer is that the porous bushing 52 allows the air in the cannula tube 20 to vent at a controlled rate. The smaller the pores, the slower the air will vent. This also controls the rate at which the pressurized blood fills the cannula. By filling the cannula slowly, turbulence is reduced. This minimizes or eliminates air bubbles that tend to cling to the side of the tube 20 when the blood is introduced rapidly.

A second advantage of the system is that the flow of blood can be controlled when the introducer is removed, since the needle 64 can be retracted from the tube while pressurized blood remains sealed in the tube by the bushing 52. The tube 20 can be clamped before the luer fitting 40 is disconnected from the male luer fitting 30. This insures that blood will not squirt out of the end of the cannula. Thus, contamination of the operator with diseased blood is avoided. A further advantage is that when the needle is retracted, as shown in FIG. 4, the point of the needle 65 is retracted into the luer 40 and this will prevent accidental contact with the point when the luer 40 is removed to allow connection with the fitting luer 30. In FIG. 6, a modified aortic root cannula, like that shown in FIGS. 2, 3 and 4, has reference characters as in these figures. A "Y" fitting 90 is formed behind the flange 24 leading to a vent tube 92 carrying a shut-off clamp 94. A male tube connector fitting 96 at the end of the tube 92 has a gas-pass, water-occluding porous plug housing 100 which contains a porous plug as previously described. This plug housing is provided to be connected to low pressure suction source to remove bubbles from the aorta during the initial insertion procedures. In FIG. 7, a section on line 7—7, the flange 24 is illustrated as well as the "Y" connection 90 and tube 92. It is important that the orientation of the "Y" connection fall between the angles "A" which is preferably about 20". The vent line 92 will prime with blood when the introducer needle is retracted and the low suction will remove bubbles from the aorta. In FIGS. 8 and 9, a modified retracting introducer is illustrated, in elevation in FIG. 8 and in section in FIG. 9. This introducer is usable as an arterial cannula and has a retracting introducer. A hollow cannula body tube 110 has on the distal end a tapered tip 112 carried on a female fitting and a proximal connector end 115. At the proximal end of the tube is a male fitting hub 116 having a forward projection inside the tube 110. A recess 120 in the proximal end of the fitting 116 contains a gas-pass, water occluding porous plug 122. A needle handle 130 is affixed to a needle shaft 132 which terminates at the distal end in an enlarged portion which slides in the end 134 of tube 110 and in the tip 112. When the needle is fully withdrawn, it can be received in the projection 118.

Thus, when the introducer needle 140 is injected into an artery, for example, the tip 112 is located within the artery and the needle can be retracted to the extent that blood can flow into the cannula body 110 and the projection 118 until it reaches the plug 122. Here it will be blocked from exiting to the outside of the cannula. The needle 140 can be withdrawn into the projection 118 and the point located within the projection to prevent contact when the hub 116 and the needle are removed to introduce the cannula into a support system.

What is claimed is as follows:

1. A method of introducing an aortic root cannula into an arterial wall of a heart preparatory to heart surgery which comprises:
   (a) introducing a distal end of a combined needle and a cannula into the heart wall,
   (b) allowing blood flow into the needle,
   (c) blocking the exit of flow from the needle with a gas-pass-water occlusion plug,
   (d) retracting the needle from the cannula,
   (e) allowing a controlled flow rate of blood into the cannula to a luer fitting at a proximal end of the cannula,
   (f) blocking the exit of flow from the cannula with a gas-pass-water occlusion plug,
   (g) clamping the cannula when filled with pressurized blood prior to disconnecting the luer fitting that contains the blood, and
   (h) connecting the cannula with a life-support conduit for the flow of cardioplegia blood.

2. A method as defined in claim 1 includes:
   (a) providing a fitting at the proximal end of the cannula to receive the distal end of the needle when retracted.

3. An introducer cannula for use with the human body which comprises:
   (a) a cannula body having an insertable tip at a distal end and a connector end at a proximal end,
   (b) a needle slidable in said body having a penetrating point projectable through said tip,
   (c) a removable fitting at the proximal end of said cannula,
   (d) a gas-pass-water occluding plug at a distal end of said fitting surrounding said needle,
   (e) a stop means adjacent the distal end of said needle to contact said plug upon withdrawal of said needle into said fitting, and
   (f) said fitting having an axial length long enough to receive the point of said needle when the needle is withdrawn prior to the removal of said needle and said fitting from said cannula.

4. An introducer cannula for use with the human body which comprises:
   (a) a cannula body having an insertable tip at a distal end and a first connector luer at a proximal end,
   (b) a second connector luer removably connectable at its distal end to said first luer,
   (c) a needle slidable within said body having a penetrating tip projectable through said cannula tip of said body,
   (d) a needle handle on a proximal end of said needle removably connectable at its distal end to a proximal end of said second luer,
   (e) means in the second lure surrounding said needle to allow gas flow through said second luer and block liquid flow, and
   (f) means in the proximal end of said needle handle to allow gas flow and block liquid flow through said needle.

5. An introducer cannula as defined in claim 4 in which said second luer has a male projection extending into a proximal end of said first luer to provide a sealed connection.

6. An introducer cannula as defined in claim 4 in which said needle handle has a transparent section to allow sight of the presence of blood in said needle handle.

7. An introducer cannula as defined in claim 4 in which full retraction of said needle prior to removal from said first and second luers places the penetrating tip of said needle within the second luer to permit removal of said first luer from said second luer without an exposed needle tip.

8. An introducer cannula as defined in claim 4 in which a suction connection in the form of a tube is provided in communication with the distal end of said cannula body, said tube having a proximal end, and a gas-pass-water occluding plug located in the proximal end of said tube, the proximal end of said tube to be connected to a source of sub-atmospheric pressure to remove air bubbles.

9. An introducer cannula for use with the human body which comprises:
   (a) a cannula body having an insertable tip at a distal end and a connector end at a proximal end,
   (b) a needle slidable in said body having a penetrating point projectable through said tip,
   (c) a removable fitting at the proximal end of said cannula,
   (d) a gas-pass-water occluding plug at a distal end of said fitting surrounding said needle,
   (e) said fitting having means to receive the point of said needle when the needle is withdrawn through the fitting prior to the removal of said needle and said fitting from said cannula, and
   (f) said fitting having also a removable male projection extending into and interfitting with the proximal end of said cannula, said needle point received in said projection so as to be unexposed when said needle and said fitting are removed from said cannula body.

* * * * *